United States Patent [19]

Rei et al.

[11] 4,049,822

[45] Sept. 20, 1977

[54] MICROBIOCIDAL COMPOSITIONS COMPRISING A SOLUTION OF A PHENOXARSINE COMPOUND

[75] Inventors: Nuno M. Rei, Peabody; Ronald C. Wilson, Wenham, both of Mass.

[73] Assignee: Ventron Corporation, Beverly, Mass.

[21] Appl. No.: 601,967

[22] Filed: Aug. 4, 1975

[51] Int. Cl.$^2$ .................................. A01N 9/00
[52] U.S. Cl. .............................. 424/297; 260/45.75 B; 424/78; 424/366
[58] Field of Search ............ 260/45.7 P, 33.4 P, 260/45.75 B; 424/297

[56] References Cited

U.S. PATENT DOCUMENTS

| | | | |
|---|---|---|---|
| 3,009,939 | 11/1961 | Friedman | 260/45.7 PH |
| 3,080,338 | 3/1963 | Nodenberg et al. | 260/45.7 PH |
| 3,689,449 | 9/1972 | Yeager et al. | 424/297 |
| 3,697,463 | 10/1972 | Oakes et al. | 260/45.7 PH |

FOREIGN PATENT DOCUMENTS 835,936    3/1970    Canada

*Primary Examiner*—Donald B. Moyer
*Attorney, Agent, or Firm*—Paul J. Cook

[57] ABSTRACT

A microbiocidal solution for resin compositions including a glycyl phosphite or glycyl phosphonate and at least about 20 weight percent of a microbiologically active phenoxarsine. The composition can include additional solvents or dispersants or resin plasticizers.

8 Claims, No Drawings

MICROBIOCIDAL COMPOSITIONS COMPRISING A SOLUTION OF A PHENOXARSINE COMPOUND

This invention relates to microbiocidal compositions containing a phenoxarsine compound and more particularly to microbiocidal solutions containing a phenoxarsine compound and a glycyl phosphite or glycyl phosphonate.

It is presently common practice to protect resin compositions from bacterial or fungal attack be incorporating a microbiocidal composition in the resin composition. These compositions prevent the deterioration of articles formed from the resin composition due to microbiological attack on the plasticizers normally incorporated into the resin to impart desirable physical properties to the article and to facilitate forming of the article.

Many of the available microbiocidal materials are solid and, in order to incorporate them homogeneously in the resin composition, it is necessary first to mix them with a liquid which solubilizes or disperses the material uniformly and thereafter, mixing the liquid composition with the resin. Unfortunately, the solubility of many of the microbiologically active material in the common solvent materials is quite low. Therefore, it is either difficult to incorporate a sufficiently high concentration of the microbiocidal material with the resin or, if sufficiently high concentrations of the active material can be incorporated in the resin, an undesirably high concentration of the solvent also must be incorporated in the resin with the resultant deterioration of the desirable characteristics of the resin composition.

Prior attempts to solve these problems have met only with limited success. For example, as disclosed in U.S. Pat. Nos. 3,689,449 issued Sept. 5, 1972 to Yeager et al. and 3,288,674, issued Nov. 29, 1966 to Yeager it has been proposed to form solutions of microbiocidal phenoxarsine compounds and a solvent having a labile hydrogen, preferably nonyl phenol, for subsequent incorporation into resin compositions. Unfortunately, the solubility of the phenoxarsines in nonyl phenol is limited to lower concentrations which necessitates incorporating nonyl phenol in higher concentration than desired in order to attain the desired phenoxarsine levels in the resin.

It would be highly desirable to provide microbiocidal compositions which contain high concentrations of a microbiocidal material. This would permit incorporating the microbiocidal composition at the desired concentration in a resin while controlling the concentration of solvent or diluent within relatively low levels in order to minimize their effect on the overall properties of the resin composition. Alternatively, it would be highly desirable to provide microbiocidal compositions which can be incorporated into resins and which also contain the usual resin modifiers such as heat stabilizers or plasticizers without adversely affecting the microbiocidal activity. This would permit incorporation of the usual resin additives with the resin in a single step.

SUMMARY OF THE INVENTION

The present invention is based upon the discovery that microbiocidal phenoxarsine compounds can be solubilized to form stable solutions with liquid compositions containing a glycyl phosphite or a glycyl phosphonate to concentrations to about 20 weight percent up to about 40 weight percent or more. The compositions of this invention also can contain other materials suitable for incorporation with resins such as plasticizers or the like or can be supplemented with the usual solvents commonly employed with phenoxarsines. These liquid phenoxarsine compositions can be incorporated into vinyl resins to impart microbiological properties thereto over extended periods of time.

DESCRIPTION OF SPECIFIC EMBODIMENTS

The microbiocidal phenoxarsines useful in the compositions of this invention are represented by the following formulae:

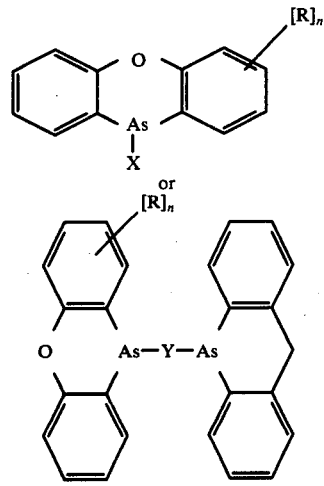

In the above formulae, X is halogen or thiocyanate, Y is oxygen or sulfur, R is halo or lower alkyl and $n$ is 0 to 3. Representative phenoxarsines useful in the present invention are 10-chlorophenoxarsine, 10-iodo-phenoxarsine, 10-bromophenoxarsine, 4-methyl-10-chlorophenoxarsine, 2-tertiary butyl-10-chlorophenoxarsine, 1,4-dimethyl-10-chlorophenoxarsine, 2-methyl-8,10-dichloro phenoxarsine, 1,3,10-trichloro phenoxarsine, 2,6,10-trichloro phenoxarsine, 2,8,10-trichloro phenoxarsine, 1,2,4,10-tetrachloro phenoxarsine, 10,10' oxybis phenoxarsine, 10-thiocyanato phenoxarsine or 10,10'-thio bis phenoxarsine. The preferred phenoxarsine is 10,10'-oxybis phenoxarsine.

The liquid phosphite solvents encompassed by the present invention are the polyether glycyl phosphites including the monophosphites, diphosphites and triphosphites as well as glycyl phosphonates. Suitable phosphites include polyalkeneglycyl phosphites such as tris (dipropyleneglycyl) phosphite, tris (triethyleneglycyl) phosphite, tetrakis (nonylphenyl) polypropyleneglycyl diphosphite, bis (neopentyl-glycyl) triethyleneglycyl diphosphite, heptakis (dipropyleneglycyl) triphosphite, poly (dipropylene glycyl-phenyl)phosphite, bis-dipropylene glycol isodecyl phosphite or the like. Representative suitable phosphonates include bis (dipropyleneglycyl) dipropyleneglycyl phosphonate or the like. The preferred glycyl phosphites are tris (dipropylene glycyl) phosphite, poly (dipropylene glycyl-phenyl) phosphite, bis (neopentylglycyl) triethylene glycyl diphosphite and tetrakis (nonylphenyl) polypropyleneglycyl diphosphite. These phosphites and phosphonates also can be employed in admixture. The phenoxarsine comprises at least about 20 weight percent and up to about 40 weight percent of the resultant solution.

In accordance with one embodiment of this invention, the glycyl phosphites or glycyl phosphonates can be employed in admixture with other liquid phosphites or with other known solvents or diluents for the phenoxarsine compounds. It has been found that the phenoxarsine compounds have limited solubility in the phosphites set forth below, when employed alone. However, when these phosphites are employed with the above-identified glycyl phosphites or glycyl phosphonates, a synergistic solvating action for the phenoxarsine compounds is obtained thereby permitting the formation of highly concentrated solutions of the phenoxarsine compounds. Suitable phosphites include the liquid alkylphosphites, arylphosphites and alkyl-arylphosphites such as dioctyl phosphite, triisodecyl phosphite, triisooctyl phosphite, trilauryl phosphite, trimethyl phosphite, diphenyl phosphite, trisnonylphenyl phosphite, triphenyl phosphite, diphenylisodecyl phosphite, diphenylisooctyl phosphite, phenyldiisodecyl phosphite, di(isooctyl)octylphenyl phosphite, mixtures thereof and the like. It has been found that these liquid phosphites can be employed with the glycyl phosphites or glycyl phosphonates to provide solutions having increased concentrations of the phenoxarsine as compared with solutions employing only the glycyl phosphite or glycyl phosphonate.

Solvents that can be employed with the glycyl phosphites or glycyl phosphonates are those having a labile hydroxyl group. Useful compounds are mono and dihydroxy compounds, for example, phenol, phenol derivatives, for example, the alkyl phenols, such as cresols, e.g., methyl phenol, 2-methyl-5-isopropyl phenol, 3-methyl-6-isopropyl phenol, and the like. Chlorinated phenols such as 4-chloro-2-phenyl-phenol, and 6-chloro-2-phenylphenol. Amino phenols such as p-aminophenol and m-aminophenol. Dihydric phenols such as catechol, resorcinol, 3,5,dihydric toluene, and the like, aliphatic alcohols having 5 to 12 carbon atoms such as 2-ethyl hexanol, octenol, 1,2,6-hexantriol, 2-methoxy methyl-2,4, dimethyl pentane diol, and the like, and monocarbocyclic acids having 5 to 12 carbon atoms such as caproic and, lauric acid, 2-ethyl hexoic acid, isotoic acid, and the like. The solvent carrier which is preferred, is a non-toxic alkyl phenol, such as nonyl phenol, dodecyl phenol, di-sec amyl phenol, and the like. The phenoxarsine-glycyl phosphite or phenoxarsine-glycyl phosphonate compositions of this invention also can be admixed with plasticizers for the resins into which the compositions are to be incorporated which plasticizers normally are not solvents for the phenoxarsine compounds. It has been found that the compositions containing the plasticizer are compatible in that the phenoxarsine compound do not precipitate or otherwise become separated from the other components in the composition. Therefore, substantial advantages are provided with these compositions since the plasticizer and the microbiocidal compound can be incorporated with the resin in one mixing step. Exemplary suitable plasticizers include diisobutyl phthalate, diisooctyl phthalate, diisodecyl phthalate, epoxidized soya or the like.

The phenoxarsine-glycyl phosphite or phenoxarsine-glycyl phosphonate solutions of the present invention contain more than about 20 weight percent phenoxarsine and preferably up to about 40 percent phenoxarsine. Prior to the present invention, phenoxarsine solutions containing more than about 20 percent phenoxarsine have not been obtainable. A further advantage results from the fact that the glycyl phosphites are not merely inert ingredients when employed with the resin but function as heat stabilizers, particularly with the vinyl resins. In addition, these solutions are more compatible with plasticizers than the other solutions available prior to the present invention in that the phenoxarsine does not become separated from solution when mixed with the plasticizer.

The glycyl phosphite-phenoxarsine or glycyl phosphonate-phenoxarsine solutions of the present invention are incorporated into a resin composition in sufficient amounts to render the resin composition stable against microbiocidal and fungicidal attack. Generally, the phenoxarsine compounds are effective in the resin at concentration of between about 100 and about 500 parts per million. The glycyl phosphite-phenoxarsine solutions are incorporated with a plasticizer in amounts between about 2.5 and about 8 weight percent preferably between about 2.5 and about 5 weight percent so that the plasticizer composition contains between about 1 and about 2 weight percent phenoxarsine and between about 2.5 and about 8 weight percent of the glycyl phophite or glycyl phosphonate either alone or incorporated with a phosphite or a solvent for the phenoxarsine.

The phenoxarsine compositions of the present invention can be employed with a wide variety of resin including the vinyl resins such as polyvinyl chloride, vinyl chloride-vinyl acetate copolymer or with polyurethane, polyethylene and polypropylene.

The following examples illustrate the present invention and are not intended to limit the same.

EXAMPLE I

The compositions set forth in Table I were prepared by first mixing the 10,10'-oxybis phenoxarsine (OBPA) with the glycyl phosphite or mixtures of the glycyl phosphite and supplementary solvent or dispersent. The resultant mixture then was agitated while being heated at 375° F. to melt the OBPA and to attain a homogeneous solution. The solutions then were cooled to room temperature and allowed to stand for 10 weeks during which time they were observed to determine their stability. Thereafter, each solution was subjected to a freeze-thaw cycle at 15° F. for 16 hours and room temperature for 8 hours on a continuous basis for a 2-week period. None of the compositions set forth in Table I experienced OBPA separation such as by crystallization or precipitation.

Table I

| | PHOSPHITE COMPOSITION, WT. % | | | | | | | | | | | | | |
|---|---|---|---|---|---|---|---|---|---|---|---|---|---|---|
| | A | B | C | D | E | F | G | H | I | J | K | L | M | N |
| Poly (dipropylene glycylphenyl) phosphite | 40 | 20 | 20 | | | | | 80 | | 37 | | 20 | | |
| Tris (dipropylene glycyl) phosphite | | | | | 60 | | | | | 37 | | | 80 | 66 |
| Bis (dipropylene glycyl) dipropylene glycyl phosphonate | | | | 60 | | | 80 | | 37 | 37 | | | | |
| Bis (neopentyl glycyl) | | | | | | 80 | | | | | | | | |

Table I-continued

| | PHOSPHITE COMPOSITION, WT. % | | | | | | | | | | | | | |
|---|---|---|---|---|---|---|---|---|---|---|---|---|---|---|
| | A | B | C | D | E | F | G | H | I | J | K | L | M | N |
| triethylene glycyl diphosphite | | | | | | | | | | | | | | |
| Diisoctyl Phosphite | 40 | 20 | 20 | | | | | | | | | 20 | | |
| Nonyl Phenol | | | 20 | | | | | | | | | | | |
| Dioctyl Phthalate | | | | | | | | | | | | 20 | | |
| OBPA | 20 | 20 | 40 | 40 | 40 | 20 | 20 | 20 | 37 | 37 | | 40 | 20 | 33 |

Each of the solutions set forth in Table I was tested for microbiological activity by measuring zones of inhibition determining minimum inhibitory concentration and, in each case, the OBPA in solution was found to be highly effective against bacteria and fungi.

EXAMPLE II

As set forth in Table II some of the compositions of Example I were admixed with a plasticizer. The OBPA-phosphite or OBPA-phosphonate solutions were added to the plasticizer at room temperature and agitated to insure uniform mixture.

Table II

| | PLASTICIZER COMPOSITION, WT. % | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Composition M | 5 | 10 | 5 | 10 | 10 | | | | | | | |
| Composition N | | | | | | 3 | 6 | 3 | 6 | 6 | | |
| Composition D | | | | | | | | | | | 2.5 | 5 |
| Composition I | | | | | | | | | | | | |
| Composition C | | | | | | | | | | | | |
| Nonyl Phenol | | | | | | | | | | | | |
| Dioctyl Phthalate | 95 | 90 | | | | 97 | 94 | | | | 97.5 | 95 |
| Diisodecyl Phthalate | | | 95 | 90 | | | | 97 | 94 | | | |
| Epoxidized Soya | | | | | 90 | | | | | 94 | | |

| | 13 | 14 | 15 | 16 | 17 | 18 | 19 | 20 | 21 | 22 | 23 | 24 | 25 |
|---|---|---|---|---|---|---|---|---|---|---|---|---|---|
| Composition M | | | | | | | | | | | | | |
| Composition N | | | | | | | | | | | | | |
| Composition D | 2.5 | 5 | 5 | | | | | | | | | | |
| Composition I | | | | 3 | 6 | 3 | 6 | 6 | | | | | |
| Composition C | | | | | | | | | 2.5 | 5 | 2.5 | 5 | 5 |
| Nonyl Phenol | | | | | | | | | 2.5 | 5 | 2.5 | 5 | 5 |
| Dioctyl Phthalate | | | | 97 | 94 | | | | 95 | 90 | | | |
| Diisodecyl Phthalate | 97.5 | 95.0 | | | | 97 | 94 | | | | 95 | 90 | 90 |
| Epoxidized Soya | | | 95.0 | | | | | 94 | | | | | |

After the observation periods, no OBPA had separated from any of the plasticizer compositions set forth in Table II. Furthermore, the microbiological properties of the OBPA were not adversely affected when incorporated with the plasticizer compositions of Table II.

Some of the plasticizer compositions were observed to form non-crystalline deposits after about 1 month after initial mixing which could be made to return to solution by heating at about 120° F.

Each of the precipitates in plasticizer solutions was examined for the presence of OBPA by Atomic Absorption after five months which showed that the precipitate is not OBPA. In all cases, the precipitate returned to solution after the solution containing the precipitate was heated to about 120° F. After this heating, the precipitate appeared after about 3 to 4 weeks. It has been determined that the presence of nonyl phenol in these compositions retards the formation of this non-crystalline precipitate at nonyl phenol concentrations of about 4% or above.

Compositions 1 through 10 remained clear and relatively free of non-crystalline deposits over the observation period. Compositions 11 through 15 also remained stable and relatively free of non-crystalline deposits but appeared somewhat hazy. Compositions 16, 17, 18 and 20 also remained stable and relatively free of non-crystalline deposits but appeared cloudy. Composition 19 remained stable and relatively free of non-crystalline deposits and appeared only slightly hazy. Compositions 21 through 25 also remained stable and relatively free of non-crystalline precipitate.

The most satisfactory solutions in that they contained little or no precipitate were compositions 6, 7 and 10.

EXAMPLE III

Plasticizer compositions 6, 7 and 10 were used to form polyvinyl chloride compositions which were tested for bacteriacidal and fungicidal activity.

Biocide compositions are evaluated using a standard PVC base compound prepared as follows:

| | |
|---|---|
| Vygen 121 (PVC resin) | 100.0 |
| Mark KBC (heat stabilizer) | 3.5 |
| Mark C (heat stabilizer) | 1.5 |
| DOP (Plasticizer) | 40.0 |
| Mark 202A (Light stabilizer) | 1.0 |
| Steric Acid (Lubricant) | 0.25 |

The above ingredients were blended using a Hobart mixer until a smooth viscous plastisol mix was obtained (usually around 30 minutes). The biocide to be tested then was incorporated into the plastisol at 100, 300 and 500 ppm levels OBPA. The treated plastisol then was cast on glass plates at a thickness of approximately 25 mils and fused in a circulating hot air oven for 10 minutes at 350° F. This casting process resulted in solid test strips which were submitted and tested for resistance against bacteria, fungas, before and after weathering for 100, 200 and 300 hours. The zones of inhibitor were measured and compared to control samples containing no biocides. In each instance, the tested composition were found to be far more effective than the control compositions.

What is claimed is:

1. A microbiocidal composition comprising a solution of above about 20 weight percent of a phenoxarsine compound of the formula selected from the group consisting of

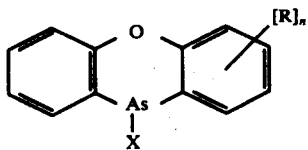

and

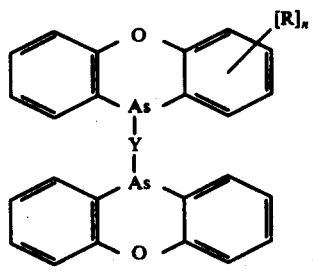

wherein X is halogen or thiocyanate and Y is oxygen or sulfur, R is lower alkyl or halogen and n is 0 to 3 and mixtures of said compounds and a solvent for the phenoxarsine selected from the group consisting of a glycyl phosphite, glycyl phosphonate and mixtures thereof.

2. The composition of claim 1 which includes a second solvent for the phenoxarsine, said second solvent selected from the group consisting of phenol, alkyl phenols, chlorinated phenols, amino phenols, dihydric phenols, aliphatic alcohols having from 5 to 12 carbon atoms and monocarboxylic acids having from 5 to 12 carbon atoms and mixtures thereof.

3. The composition of claim 2 wherein the second solvent is nonyl phenol.

4. The composition of claim 1 wherein the solvent is tris(dipropyleneglycyl) phosphite.

5. The composition of claim 3 wherein the solvent is tris(dipropyleneglycyl) phosphite.

6. The composition of claim 4 wherein the phenoxarsine compound is 10,10'-oxybis phenoxarsine.

7. The composition of claim 5 wherein the phenoxarsine compound is 10,10'-oxybis phenoxarsine.

8. A microbiocidal composition comprising a solution of above about 20 weight percent of 10,10'-oxybis phenoxarsine and a solvent for the phenoxarsine selected from the group consisting of a glycyl phosphite, a glycyl phosphonate and mixtures thereof.

* * * * *